United States Patent
Craun et al.

(10) Patent No.: US 9,469,785 B2
(45) Date of Patent: Oct. 18, 2016

(54) AQUEOUS COATING COMPOSITIONS INCLUDING THE REACTION PRODUCT OF MALEIC ANHYDRIDE WITH AN UNSATURATED COMPOUND AND AN AMINE

(71) Applicant: Akzo Nobel Coatings International B.V., Arnhem (NL)

(72) Inventors: Gary Pierce Craun, Berea, OH (US); Jude Rademacher, Akron, OH (US); Patricia Geelen, Heerlen (NL)

(73) Assignee: AKZO NOBEL COATINGS INTERNATIONAL B.V., Arnhem (NL)

( * ) Notice: Subject to any disclaimer, the term of this patent is extended or adjusted under 35 U.S.C. 154(b) by 38 days.

(21) Appl. No.: 14/428,523

(22) PCT Filed: Sep. 19, 2013

(86) PCT No.: PCT/EP2013/069423
§ 371 (c)(1),
(2) Date: Mar. 16, 2015

(87) PCT Pub. No.: WO2014/044732
PCT Pub. Date: Mar. 27, 2014

(65) Prior Publication Data
US 2015/0247061 A1      Sep. 3, 2015

Related U.S. Application Data

(60) Provisional application No. 61/702,789, filed on Sep. 19, 2012, provisional application No. 61/815,814, filed on Apr. 25, 2013.

(30) Foreign Application Priority Data

Oct. 11, 2012  (EP) ................................. 12188180

(51) Int. Cl.
C09D 191/00   (2006.01)
C09D 5/00     (2006.01)
(Continued)

(52) U.S. Cl.
CPC ........... *C09D 191/005* (2013.01); *B65D 23/02* (2013.01); *C07D 207/40* (2013.01);
(Continued)

(58) Field of Classification Search
None
See application file for complete search history.

(56) References Cited

U.S. PATENT DOCUMENTS 2,262,923 A    11/1941  Clocker
2,977,334 A *  3/1961   Zopf, Jr. .................. C08F 8/00
                                                          524/531
(Continued)

FOREIGN PATENT DOCUMENTS

DE    3632277 A1   4/1988
DE    10142991 C2  4/2003
(Continued)

OTHER PUBLICATIONS

Badulescu et al., Chemical Transformation of Poly(Styrene-Alt-Maleic Anhydride) With p-Amino-N, N-Diethylaniline, Revue Romaine de chimie, 2008 53(6), 489-496.
(Continued)

*Primary Examiner* — Robert S Loewe
(74) *Attorney, Agent, or Firm* — Alice C. Su

(57) ABSTRACT

The invention includes an aqueous coating composition having a substituted succinimide compound, wherein the substituted succinimide compound has an acid value of at least about 30 mg KOH/g of the substituted succinimide compound. The substituted succinimide compound may be the reaction product of an unsaturated oil comprising at least one non-aromatic unsaturated carbon-carbon bond, a polymer derived from the unsaturated oil, or a combination thereof with maleic anhydride and a primary amine.

10 Claims, 1 Drawing Sheet

(51) Int. Cl.

| | | |
|---|---|---|
| C09D 7/00 | (2006.01) | |
| C09D 7/02 | (2006.01) | |
| C09F 7/00 | (2006.01) | |
| C07D 207/40 | (2006.01) | |
| C07D 207/408 | (2006.01) | |
| B65D 23/02 | (2006.01) | |
| C23F 11/00 | (2006.01) | |
| C09D 125/08 | (2006.01) | |
| C09D 133/00 | (2006.01) | |
| C09D 163/00 | (2006.01) | |
| C09D 173/02 | (2006.01) | |
| C09D 175/04 | (2006.01) | |

(52) U.S. Cl.
CPC ............ *C07D207/408* (2013.01); *C09D 5/00* (2013.01); *C09D 7/00* (2013.01); *C09D 7/02* (2013.01); *C09D 125/08* (2013.01); *C09D 133/00* (2013.01); *C09D 163/00* (2013.01); *C09D 173/02* (2013.01); *C09D 175/04* (2013.01); *C09F 7/00* (2013.01); *C23F 11/00* (2013.01)

(56) References Cited

U.S. PATENT DOCUMENTS

| | | | |
|---|---|---|---|
| 3,293,201 A | | 12/1966 | Shahade et al. |
| 4,548,724 A | * | 10/1985 | Karol ................ C07D 207/412 508/291 |
| 4,618,655 A | | 10/1986 | Dehm et al. |
| 4,855,215 A | * | 8/1989 | Nakano ................ C08F 290/12 430/283.1 |
| 4,962,149 A | * | 10/1990 | Fry ........................ C09D 7/125 524/532 |
| 4,988,759 A | * | 1/1991 | Den Hartog ......... C08K 5/5435 524/264 |
| 5,466,753 A | * | 11/1995 | Marczinke ............ C08F 255/00 525/193 |
| 5,519,081 A | * | 5/1996 | Ashton .................. C08C 19/25 524/264 |
| 6,160,055 A | | 12/2000 | Camberlin et al. |
| 6,184,303 B1 | | 2/2001 | Camberlin et al. |
| 6,353,060 B1 | | 3/2002 | Paulen et al. |
| 6,441,213 B1 | * | 8/2002 | Musa .................... C07F 7/1836 556/418 |
| 8,476,404 B1 | * | 7/2013 | Lele ...................... C07K 17/06 424/78.27 |
| 2002/0128342 A1 | * | 9/2002 | Xu ............................ C08F 8/00 522/35 |
| 2003/0236356 A1 | * | 12/2003 | Syed ........................ C08F 8/32 525/333.7 |
| 2007/0129474 A1 | * | 6/2007 | Salamone ............... A61L 15/26 524/261 |
| 2009/0029155 A1 | | 1/2009 | Gothlich et al. |
| 2009/0065736 A1 | * | 3/2009 | Johnson .................... C11C 3/00 252/88.1 |
| 2010/0099813 A1 | | 4/2010 | Gobelt et al. |

FOREIGN PATENT DOCUMENTS

| | | |
|---|---|---|
| WO | WO 2009/006527 A1 | 1/2009 |
| WO | WO 2013/123314 A1 | 8/2013 |

OTHER PUBLICATIONS

Latov et al., Synthesis of Optically Active I-Alanine Maleimide-Styrene Copolymers, Institute of Heteroorganic Compounds, Academy of Sciences of USSR. No. 9, pp. 2036-2041, Sep. 1972.

* cited by examiner

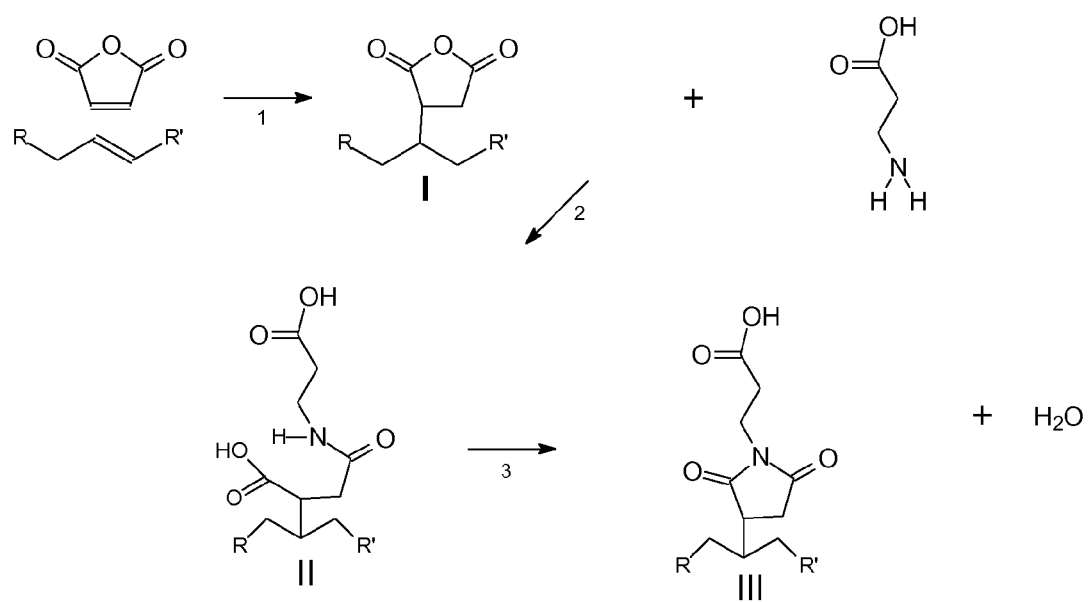

AQUEOUS COATING COMPOSITIONS INCLUDING THE REACTION PRODUCT OF MALEIC ANHYDRIDE WITH AN UNSATURATED COMPOUND AND AN AMINE

This application is the National Stage of International Application No. PCT/EP2013/069423, filed Sep. 19, 2013, which claims to the benefit of U.S. Provisional Patent Application Nos. 61/702,789 and 61/815,814, filed Sep. 19, 2012 and Apr. 25, 2013, respectively, and also claims the benefit of European Patent Application No. 12188180.9, filed Oct. 11, 2012, the contents of which are herein incorporated by reference.

BACKGROUND OF THE INVENTION

1. Field of the Invention

The present invention relates to coating compositions including a substituted succinimide compound, methods of preparing the coating compositions, substrates coated with the coating compositions, and methods of coating substrates with the coating compositions.

2. Description of Related Art

Coating compositions formed from epoxy resins have been used to coat packaging and containers for foods and beverages. Although the weight of scientific evidence, as interpreted by the major global regulatory food safety agencies in the US, Canada, Europe, and Japan, shows that the levels of bisphenol A consumers are exposed to with current commercial epoxy based coatings is safe, some consumers and brand owners continue to express concern about safety. Coating compositions that do not contain bisphenol-A or any other possible endocrine disruptor are desirable. In addition, styrene monomers and copolymers of styrene and maleic anhydride have been widely used in coating compositions that protect food and beverages to improve corrosion resistance and adhesion to metal, but it has been recently desirable to produce such coating compositions without styrene.

SUMMARY OF THE INVENTION

Carbon dioxide present in soft drinks is known to penetrate packaging coating compositions possibly leading to coating delamination. We have discovered that incorporating a certain substituted succinimide compound into the coating composition provides excellent resistance to delamination as well as improved adhesion and corrosion resistance on metallic substrates.

The invention relates to coating compositions including a substituted succinimide compound, methods of preparing the coating compositions, substrates coated with the coating compositions, and methods of coating substrates with the coating compositions. The coating compositions may be aqueous protective coating packaging compositions that exhibit improved adhesion and corrosion resistance when applied to metallic substrates, such as aluminium, steel or electrocoated tin plate steel. The coating compositions can be applied directly to the metallic substrate to provide a protective layer against contact with the metallic substrate.

In some embodiments of the invention, there is provided an aqueous coating composition comprising a substituted succinimide compound. The substituted succinimide compound may have an acid value of at least about 30 mg KOH/g of the substituted succinimide compound. The substituted succinimide compound may be the reaction product of an unsaturated oil comprising at least one non-aromatic unsaturated carbon-carbon bond, a polymer derived from the unsaturated oil, or a combination thereof with maleic anhydride and a primary amine.

Method of preparing an aqueous coating composition are also disclosed. The methods may comprise the steps of a) reacting an unsaturated oil comprising at least one non-aromatic unsaturated carbon-carbon bond, a polymer derived from the unsaturated oil, or a combination thereof with maleic anhydride to form a substituted succinic anhydride compound, b) reacting the substituted succinic anhydride compound with a primary amine to form an amic acid intermediate, c) evolving water from the amic acid intermediate to form a substituted succinimide compound, and d) neutralizing the substituted succinimide compound in the presence of water to form the aqueous coating composition. The substituted succinimide compound may have an acid value of at least about 30 mg KOH/g of the substituted succinimide compound.

BRIEF DESCRIPTION OF THE DRAWINGS

FIG. 1 shows a reaction scheme to form a substituted succinimide compound where the primary amine is the amino acid is β-alanine.

DETAILED DESCRIPTION OF THE INVENTION

The invention relates to coating compositions including a substituted succinimide compound, methods of preparing the coating compositions, substrates coated with the coating compositions, and methods of coating substrates with the coating compositions. The coating compositions may be aqueous protective packaging coating compositions that exhibit improved adhesion and corrosion resistance when applied to metallic substrates, such as aluminium, steel or electrocoated tin plate steel. In addition, the coating compositions may be prepared from renewable materials such as vegetable oils and amino acids and do not have the health concerns associated with epoxy resins and styrene-based compounds. The coating compositions can be applied directly to the metallic substrate to provide a protective layer against contact with the metallic substrate.

In some embodiments of the invention, there is provided an aqueous coating composition comprising a substituted succinimide compound. The substituted succinimide compound may have an acid value of at least about 30 mg KOH/g of substituted succinimide compound. In some embodiments, the substituted succinimide compound may comprise from greater than 0 to about 10 wt % of the coating composition. If the percentage of the substituted succinimide compound is above about 10 wt %, the adhesion of the coating composition to the metallic substrate might deteriorate, while a percentage below about 0.1 wt % might not appreciably benefit corrosion resistance.

The substituted succinimide compound may be the reaction product of an unsaturated oil comprising at least one non-aromatic unsaturated carbon-carbon bond, a polymer derived from the unsaturated oil, or a combination thereof, with maleic anhydride and a primary amine. The reaction of maleic anhydride with the unsaturated oil or the polymer derived from the unsaturated oil may occur by the Diels-Alder reaction or the Alder-ene reaction.

The unsaturated oil and the polymer derived from the unsaturated oil may have one or more unsaturated carbon-carbon bonds. The unsaturated carbon-carbon bond may be a double bond. The double bonds may be singly-unsaturated (containing only one double bond) or multi-unsaturated (containing more than one double bond). The unsaturated oil and the polymer derived from the unsaturated oil may be a multi-unsaturated compound containing conjugated and/or non-conjugated double bonds.

The unsaturated oil and the polymer derived from the unsaturated oil can be prepared for non-limiting example by esterification of one or more polyols, polycarboxylic acids, fatty acids, and mixtures thereof. At least part of the unsaturated oil and the polymer derived from the unsaturated oil may be oxidatively drying as a result of the incorporation of unsaturated aliphatic compounds, such as unsaturated fatty acids. Suitable examples of unsaturated fatty acids include myristoleic acid, palmitoleic acid, oleic acid, gadoleic acid, erucic acid, ricinoleic acid, oleic acid, linoleic fatty acid, linolenic fatty acid, tall oil fatty acid, sunflower fatty acid, safflower fatty acid, soybean oil fatty acid, and the like. Examples of fatty acids containing conjugated double bonds include dehydrated castor oil fatty acid and wood oil fatty acid. Monocarboxylic acids suitable for use include tetrahydrobenzoic acid and hydrogenated or non-hydrogenated abietic acid or its isomer. If so desired, the monocarboxylic acids may be used wholly or in part as triglyceride, for example as a vegetable oil, in the preparation of the unsaturated oil and the polymer derived from the unsaturated oil. If so desired, mixtures of two or more of such monocarboxylic acids or triglycerides may be employed, optionally in the presence of one or more saturated, (cyclo)aliphatic or aromatic monocarboxylic acids, for example, pivalic acid, 2-ethylhexanoic acid, lauric acid, palmitic acid, stearic acid, 4-tert-butyl-benzoic acid, cyclopentane carboxylic acid, naphthenic acid, cyclohexane carboxylic acid, 2,4-dimethyl benzoic acid, 2-methyl benzoic acid, and benzoic acid.

Polycarboxylic acids may also be incorporated into the unsaturated oil and the polymer derived from the unsaturated oil, such as phthalic acid, isophthalic acid, terephthalic acid, 5-tert-butyl isophthalic acid, trimellitic acid, pyromellitic acid, succinic acid, adipic acid, 2,2,4-trimethyl adipic acid, azelaic acid, sebacic acid, dimerized fatty acids, cyclopentane-1,2-dicarboxylic acid, cyclohexane-1,2-dicarboxylic acid, 4-methylcyclohexane-1,2-dicarboxylic acid, tetrahydrophthalic acid, butane-1,2,3,4-tetracarboxylic acid, endoisopropylidene-cyclohexane-1,2-dicarboxylic acid, cyclohexane-1,2,4,5-tetracarboxylic acid, and butane-1,2,3,4-tetracarboxylic acid. If so desired, the carboxylic acids may be used as an anhydride or in the form of an ester, for example, an ester of an alcohol having 1-4 carbon atoms.

The unsaturated oil and the polymer derived from the unsaturated oil may further comprise polyol building blocks. Examples of suitable polyols include ethylene glycol, 1,3-propane diol, 1,6-hexane diol, 1,12-dodecane diol, 3-methyl-1,5-pentane diol, 2,2,4-trimethyl-1,6-hexane diol, 2,2-dimethyl-1,3-propane diol, and 2-methyl-2-cyclohexyl-1,3-propane diol. Examples of suitable triols include glycerol, trimethylol ethane, and trimethylol propane. Suitable polyols having more than three hydroxyl groups include pentaerythritol, sorbitol, and etherification products, such as ditrimethylol propane and di-, tri-, and tetrapentaerythritol.

The unsaturated oil and the polymer derived from the unsaturated oil can be obtained by direct esterification of the constituent components, with the option of a portion of these components having been pre-converted into ester diols or polyester diols. In some embodiments, the unsaturated oil and the polymer derived from the unsaturated oil can be added in the form of a drying oil, such as linseed oil, fish oil, or dehydrated castor oil. The unsaturated oil and the polymer derived from the unsaturated oil may be produced by transesterification with other acids and polyols at a temperature in the range of about 200 to about 250 C, optionally in the presence of solvents such as toluene and/or xylene.

Suitable examples of polymers derived from unsaturated oils include alkyd resins. Such alkyd resins can be polyesters modified with unsaturated fatty acids or unsaturated oils comprising unsaturated fatty acids.

Primary amines in some embodiments may have the general formula $NH_2RCOOH$, where R can be an alkyl group or aryl group with about 2 to about 30 carbon atoms or preferably about 3 to about 12 carbon atoms. Non-limiting examples of suitable primary amines include without limitation glycine, β-alanine, arginine, asparagine, cysteine, leucine, glutamine, 5-aminopentanoic acid, 7-aminoheptanoic acid, 8-aminooctanoic acid, 6-aminohexanoic acid, 3-aminobutanoic acid, and mixtures thereof. The acid group and the amine group of the amino acid may be separated by more than one carbon atom, since such amino acids are typically more reactive than when the groups are separated by only one carbon atom.

The acid value of the substituted succinimide compound should be sufficient to enable the substituted succinimide compound to be dispersible or soluble in an aqueous medium after neutralization. The solubility of the substituted succinimide compound might depend at least in part on the hydrophobicity of the substituted succinimide compound itself, its molecular weight, as well as the nature of the aqueous medium. In some embodiments, the number average molecular weight of the substituted succinimide compound is from about 400 to about 10,000 Daltons, or from about 700 to about 3000 Daltons. The number average molecular weight described herein is measured by gel permeation chromatography, which is sometimes referred to as called size exclusion chromatography, with a polystyrene standard. In some embodiments, the acid value of the substituted succinimide compound is from about 30 to about 300 mg KOH/g of the substituted succinimide compound or from about 50 to about 150 mg KOH/g of the substituted succinimide compound. The acid value described herein is measured by ASTM D1639 titled "Standard test method for Acid value of Organic Coating Materials".

The primary amine does not necessarily need to contain an acid group when the unsaturated oil or polymer derived from the unsaturated oil contains an acid group, such as for example when polymer is an unsaturated fatty acid. However, the unsaturated oil, the polymer derived from the unsaturated oil and the primary amine may all include acid groups.

The aqueous coating compositions of the invention in certain embodiments may have a continuous phase having at least 50% water or at least 65% water. Suitable solvents may include n-butanol, ethylene glycol mono-butyl ether, and the like. The remainder of the continuous phase may comprise organic solvents, which may be water soluble, partly water soluble or water insoluble.

The substituted succinimide compound in certain embodiments may be partially or fully neutralized to facilitate dispersion in the continuous phase of the aqueous coating composition. Suitable neutralising agents include without limitation ammonia, an amine, an alkali metal base, and mixtures thereof. Suitable amines include without limitation dimethyl amino ethanol, triethylamine, amino-2-methyl propanol, dimethyl amino propanol, dimethyl amino-2-methyl propanol, and mixtures thereof. Suitable alkali metal bases include without limitation potassium hydroxide, sodium hydroxide, and mixtures thereof.

The aqueous coating composition in certain embodiments may include a binder polymer. In certain embodiments, the binder polymer may be present in an amount of at least about 50 wt % or from about 90 to about 99.9 wt % of the coating composition. Suitable binder polymers include without limitation an acrylic polymer, a styrene-acrylic polymer, a polyurethane polymer, an alkyd polymer, an epoxy polymer, and mixtures and/or hybrid copolymers thereof. Aqueous coating compositions in certain embodiments having the binder polymer may form a coherent film at ambient temperatures of from about 0 to about 40° C. or when baked at temperatures ranging from about 130 to about 250° C.

The binder polymer can comprise an aqueous dispersion of particles formed using known emulsion polymerization processes, such as latex polymerization, mini-emulsion polymerization, or microsuspension polymerization. Such dispersions are often referred to as latex dispersions. Alternatively, an emulsion of polymer in an aqueous medium can be made by emulsifying the binder polymer with or without a solvent and optionally in the presence of a surfactant. Suitable monomers to prepare the binder polymer include for non-limiting example styrene, alpha-methyl styrene and the like, as well as mixtures thereof; alkyl esters of acrylic or methacrylic acid, such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, decyl acrylate, benzyl methacrylate, isobutyl methacrylate and isobornyl methacrylate; hydroxyalkyl esters of the foregoing acids, such as 2-hydroxyethyl acrylate, 2-hydroxyethyl methacrylate, and 2-hydroxypropyl methacrylate, glycidyl acrylate, glycidyl methacrylate, acrylic acid and methacrylic acid; polyacrylates, such as butanediol dimethacrylate; and mixtures of the foregoing.

Without being bound to any theory, the inventors believe there are two characteristics of the substituted succinimide compound which cause it to function as an adhesion promoter for coating compositions, namely, the binding sites of the substituted succinimide compound and the hydrophobic character of the substituted succinimide compound. The imide and the carboxy groups of the substituted succinimide compound both help to bind the coating composition to the metal substrate, and having multiple binding sites provides better binding strength. One can easily achieve multiple binding sites with higher molecular weight compounds. As the molecular weight increases, the hydrophobic portion of the substituted succinimide compound interacts with the binder polymer to help prevent the binder polymer from de-bonding from the substituted succinimide compound. If the molecular weight is too high, the chance for incompatibility with some binder polymers might increase.

FIG. 1 shows the steps of a reaction scheme to form a substituted succinimide compound where the primary amine is the amino acid β-alanine. Step 1 is the reaction of an unsaturated carbon chain with maleic anhydride to form the substituted succinic anhydride compound (I). Step 2 shows the reaction of the substituted succinic anhydride compound (I) with β-alanine to form an amic acid intermediate (II). The amic acid intermediate (II) loses water in step 3 to form the substituted succinimide compound (III).

The invention also includes methods of coating a substrate comprising the step of applying a coating composition of the invention to the substrate. Substrates coated with such coating compositions are also included. A method of preparing the aqueous coating composition may comprise the steps of a) reacting an unsaturated oil comprising at least one non-aromatic unsaturated carbon-carbon bond, a polymer derived from the unsaturated oil, or a combination thereof with maleic anhydride to form a substituted succinic anhydride compound, b) reacting the substituted succinic anhydride compound with a primary amine to form an amic acid intermediate, c) evolving water from the amic acid intermediate to form a substituted succinimide compound, and d) neutralizing the substituted succinimide compound in the presence of water to form the aqueous coating composition. In some embodiments, aqueous coating composition further comprises a binder polymer.

In certain embodiments of the invention, the unsaturated oil or polymer derived from the unsaturated oil can be heated in the presence of maleic anhydride to attach the maleic anhydride to the unsaturated oil or polymer derived from the unsaturated oil by an Alder-Ene reaction to form a substituted succinic anhydride compound. A primary amine is then added to the substituted succinic anhydride compound to form an amic acid intermediate. As the mixture is gradually heated, water is evolved to yield a substituted succinimide compound. After cooling, a solvent and/or a neutralizing base can be added with water to the substituted succinimide compound to form an aqueous dispersion. Thereafter, the aqueous dispersion of the substituted succinimide compound can be mixed with a binder polymer to form a coating composition of the invention.

For non-limiting example, soybean oil can be heated in the presence of maleic anhydride to about 225° C. to attach the anhydride to the soybean oil by an Alder-Ene reaction to form a substituted succinic anhydride soybean oil intermediate. β-alanine can be added to the mixture at about 140° C. to form an amic acid intermediate. As the mixture is gradually heated to about 170° C., water is evolved to yield the soybean oil substituted succinimide compound. After cooling to about 100° C., a neutralizing base such as a tertiary amine or ammonia can be added with water to form an aqueous dispersion of the soybean oil substituted succinimide compound. Thereafter, the aqueous dispersion of the soy bean oil substituted succinimide compound can be mixed with a binder polymer to form a coating composition of the invention.

The coating compositions of the invention may include conventional additives known to those skilled in the art, such as without limitation, flow agents, surface active agents, defoamers, anti-cratering additives, lubricants, meat-release additives, and cure catalysts.

One or more coating compositions of the invention are applied to a substrate in some embodiments, such as for non-limiting example, cans, metal cans, packaging, containers, receptacles, can ends, or any portions thereof used to hold or touch any type of food or beverage. In some embodiments, one or more coatings are applied in addition to the coating composition of the present invention, such as for non-limiting example, a prime coat may be applied between the substrate and a coating composition of the present invention.

The coating compositions can be applied to substrates in any manner known to those skilled in the art. In some embodiments, the coating compositions are sprayed onto a substrate. When spraying, the coating composition may contain, for non-limiting example, about 10% and about 30% by weight polymeric solids relative to about 70% to about 90% water including other volatiles such as, without limitation, minimal amounts of solvents, if desired. For some applications, typically those other than spraying, the aqueous polymeric dispersions can contain, for non-limiting example, about 20% and about 60% by weight polymer solids. Organic solvents are utilized in some embodiments to facilitate spray or other application methods and such solvents include, without limitation, n-butanol, 2-butoxy-ethanol-1, xylene, toluene, and mixtures thereof. In some embodiments, n-butanol is used in combination with 2-butoxy-ethanol-1.

The coating compositions of the present invention may be pigmented and/or opacified with known pigments and opacifiers in some embodiments. For many uses, including food use for non-limiting example, the pigment is titanium dioxide. The resulting aqueous coating composition may be applied in some embodiments by conventional methods known in the coating industry. Thus, for non-limiting example, spraying, rolling, dipping, and flow coating application methods can be used for both clear and pigmented films. In some embodiments, after application onto a substrate, the coating may be cured thermally at temperatures in the range from about 130° C. to about 250° C., and alternatively higher for time sufficient to effect complete curing as well as volatilizing of any fugitive component therein.

For substrates intended as beverage containers, the coating compositions may be applied in some embodiments at a rate in the range from about 0.5 to about 15 milligrams of polymer coating per square inch of exposed substrate surface. In some embodiments, the water-dispersible coating is applied at a thickness between about 1 and about 25 microns.

EXAMPLES

The invention will now be illustrated by the following examples.

Tests

The acid value was measured by dissolving about 0.1 g of the sample in a 1:1 mixture of xylene and isopropanol. One drop of phenolphthalein in ethanol was added to the resulting mixture. The mixture was then titrated to a light pink end point using a 0.1 normal potassium hydroxide solution.

Example 1

Step 1—Preparation of the Substituted Succinic Anhydride Compound 150.0 g of soybean oil, 3.0 g of xylene and 50.0 g of maleic anhydride were added (under a nitrogen blanket) to a 1 liter flask (equipped with a stirrer and a reflux condenser). While stirring the temperature was raised to 180° C. and then further increased to 220° C. over 45 minutes. The temperature was held for 1.5 hours after which time the mixture was cooled to 100° C. The xylene washed down subliming maleic anhydride and thus gave better conversion and a cleaner reaction. The xylene distilled off in Step 2 with the water.

Step 2—Conversion of the Substituted Succinic Anhydride Compound to a Substituted Succinimide Compound The reflux condenser was removed from the flask and replaced with a Dean and Stark condenser allowing vapor to be removed and collected from the flask. 45.5 g of β-alanine was added to the substituted succinic anhydride compound and the temperature was increased to 170° C. over 1 hour. The resulting exotherm and foam from the reaction of the maleic anhydride and the primary amine were controlled. As foaming subsided at 170° C., a vacuum was applied to drive the reaction to completion. About 7 g of water were collected over about 2 hours at 170° C. as the substituted succinimide compound was formed.

Step 3—Formation of a Dispersion

The substituted succinimide compound was cooled to about 90° C., and 35 g of dimethylethanol amine dissolved in 100 g was added over about 2 minutes. A further 408 g of water was added over about 15 minutes with agitation (400 rpm, 3 inch flat blade) as the dispersion was formed and cooled. The solids content of the dispersion was 20.4%.

Example 2

The same procedure was followed as in Example 1, except that the 150.0 g of soybean oil was replaced with 135.0 g of gum rosin, the 50.0 g of maleic anhydride was replaced with 45.0 g of maleic anhydride, the 45.5 g of β-alanine was replaced with 41.0 g of β-alanine, the 35 g of dimethyl amino ethanol was replaced with 33 g of dimethyl amino ethanol, and the 408 g of water was replaced with 602 g of water.

Example 3

The following ingredients were reacted according to the method described below.

|  | g | mol |
| --- | --- | --- |
| Soy bean oil | 150.0 | 0.17 |
| Xylene | 3.0 |  |
| Maleic anhydride | 50.0 | 0.51 |
| β-alanine | 45.5 | 0.51 |

Step 1—Preparation of the Substituted Succinic Anhydride Compound

The soybean oil, xylene and maleic anhydride were added (under a nitrogen blanket) to a 1 liter flask (equipped with stirrer and condenser) whilst stirring. The temperature was raised to 180° C. and then further increased to 220° C. over 45 minutes. This temperature was held for 1.5 hours after which time the mixture was cooled to 100° C. Note: the xylene washes down subliming maleic anhydride and thus gives better conversion and a cleaner reaction. It distilled off in step 2 with the water.

Step 2—Conversion of the Substituted Succinic Anhydride Compound to a Substituted Succinimide Compound The reflux condenser was removed from the flask and replaced with a Dean and Stark condenser allowing vapors to be removed and collected from the flask. β-alanine was added and the temperature increased to 170° C. over 1 hour. Care was required to control the resulting exotherm and foaming from the reaction of the anhydride and the amine. As foaming subsided, at 170° C. a vacuum was applied to drive the reaction forward. About 7 grams of water was collected over about 2 hours at 170° C. as the substituted succinimide compound was formed.

Step 3—Formation of an Emulsion

The substituted succinimide compound was cooled to about 90° C., and 35 grams of dimethylethanol amine dissolved in 100 grams was added over about 2 minutes. A further 408 grams of water was added over about 15 minutes with good agitation (400 rpm, 3 inch flat blade) as the emulsion was formed and cooled. The solids content of the emulsion was 20.4%.

Example 4

The following ingredients were reacted according to the method described below.

|  | g | mol |
|---|---|---|
| Setal276 XX-98 | 200.0 |  |
| Xylene | 3.0 |  |
| Maleic anhydride | 50.0 | 0.51 |
| β-alanine | 45.5 | 0.51 |

Step 1—Preparation of the Substituted Succinic Anhydride Compound

The soybean oil, xylene and maleic anhydride were added (under a nitrogen blanket) to a 1 liter flask (equipped with stirrer and condenser) whilst stirring. The temperature was raised to 180° C. and then further increased to 220° C. over 45 minutes. This temperature was held for 1.5 hours after which time the mixture was cooled to 100° C. Vacuum was applied.

Step 2—Conversion of the Substituted Succinic Anhydride Compound to a Substituted Succinimide Compound The reflux condenser was removed from the flask and replaced with a Dean and Stark condenser allowing vapors to be removed and collected from the flask. β-alanine was added and the temperature was increased to 150° C. over 1 hour. Care was required to control the resulting exotherm and foaming from the reaction of the anhydride and the amine.

Step 3—Formation of an Emulsion

The substituted succinimide compound was cooled to about 90° C., and 35 grams of dimethylethanol amine dissolved in 100 g was added over about 2 minutes. A further 408 grams of water was added over about 15 minutes with good agitation (400 rpm, 3 inch flat blade) as the emulsion was formed and cooled. The solids content of the emulsion was 20.4%.

The invention claimed is:

1. An aqueous coating composition comprising a substituted succinimide compound, wherein the substituted succinimide compound has an acid value of at least about 30 mg KOH/g of the substituted succinimide compound, and wherein the substituted succinimide compound is the reaction product of
    a) an unsaturated oil comprising at least one non-aromatic unsaturated carbon-carbon bond, a polymer derived from the unsaturated oil, or a combination thereof;
    b) maleic anhydride; and
    c) a primary amine of general formula $NH_2RCOOH$, wherein R is an alkyl group or an aryl group with about 2 to about 30 carbon atoms and wherein the amine (—$NH_2$) group and the acid (—COOH) group of the primary amine are separated by more than one carbon atom.

2. The aqueous coating composition according to claim 1, wherein the aqueous coating composition further comprises a binder polymer, and wherein the substituted succinimide compound comprises from greater than 0 to about 10 wt % of the coating composition.

3. The aqueous coating composition according to claim 2, wherein the binder polymer comprises an acrylic polymer, a styrene-acrylic polymer, a polyurethane polymer, an alkyd polymer, an epoxy polymer, or a mixture or hybrid copolymer thereof.

4. The aqueous coating composition according to claim 1, wherein the number average molecular weight of the substituted succinimide compound is from about 400 to about 10,000 Daltons.

5. The aqueous coating composition according to claim 1, wherein the acid value of the substituted succinimide compound is from about 30 to about 300 mg KOH/g of the substituted succinimide compound.

6. The aqueous coating composition according to claim 1, wherein the substituted succinimide compound is partially or fully neutralized to facilitate dispersion in the aqueous coating composition.

7. The aqueous coating composition according to claim 1, wherein the primary amine is β-alanine.

8. The aqueous coating composition according to claim 1, wherein R is substituted with an acid group.

9. A substrate coated with the aqueous coating composition according to claim 1.

10. A method of preparing an aqueous coating composition comprising:
    a) reacting an unsaturated oil comprising at least one non-aromatic unsaturated carbon-carbon bond, a polymer derived from the unsaturated oil, or a combination thereof with maleic anhydride to form a substituted succinic anhydride compound;
    b) reacting the substituted succinic anhydride compound with a primary amine of general formula $NH_2RCOOH$, where R is an alkyl group or an aryl group with about 2 to about 30 carbon atoms and wherein the amine (—$NH_2$) group and the acid (—COOH) group of the primary amine are separated by more than one carbon atom to form an amic acid intermediate;
    c) evolving water from the amic acid intermediate to form a substituted succinimide compound; and
    d) neutralizing the substituted succinimide compound in the presence of water to form the aqueous coating composition,
    wherein the substituted succinimide compound has an acid value of at least about 30 mg KOH/g of the substituted succinimide compound.

* * * * *